US005958750A

United States Patent [19]

Au-Young et al.

[11] Patent Number: 5,958,750

[45] Date of Patent: Sep. 28, 1999

[54] HUMAN HYALURONIDASE

[75] Inventors: Janice Au-Young, Berkeley; Phillip R. Hawkins, Mountain View; Jennifer L. Hillman, San Jose, all of Calif.

[73] Assignee: Inctye Pharmaceuticals, Inc., Palo Alto, Calif.

[21] Appl. No.: 08/675,507

[22] Filed: Jul. 3, 1996

[51] Int. Cl.[6] .............................. C12N 9/26; C12N 15/11; C12N 15/63; C12N 15/85

[52] U.S. Cl. ........................ 435/201; 435/320.1; 435/325; 536/23.2

[58] Field of Search ........................ 536/23.2; 435/320.1, 435/240.2, 69.1, 201

[56] References Cited

PUBLICATIONS

Klocker, J. et al., "Combined Application of Cisplatin, Vindesine, Hyaluronidase and Radiation for Treatment of Advance Squamous Cell Carcinoma of the Head and Neck", *Am J. Clin Oncol*, 1995 vol. 18, pp. 425–428.

Laurent, T.C. et al., "Hyaluronan", *FASEB J*, (1992) vol. 6, pp. 2397–2404.

Lin, Y. et al., "Molecular Cloning of the Human and Monkey Sperm Surface Protein PH–20", *Proc. Natl. Acad. Sci. USA*, 1993 vol. 90, pp. 10071–10075.

Lin, Y. et al.; "A Hyaluronidase Activity of the Sperm Plasma Membrane Protein PH–20 Enables Sperm to Penetrate the Cumulus Cell Layer Surrounding the Egg", *J. Cell Biol.*, (1994) vol. 125, pp. 1157–1163.

Lokeshwar, V.B., et al., "Association of Elevated Levels of Hyaluronidase, a Matrix–Degrading Enzyme, with Prostate Cancer Progression", *Cancer Res.*, 1996, vol. 56, pp. 651–657.

Lu, G. et al., "Sequence Identity and Antigenic Cross–reactivity of White Face Hornet Venom Allergen, Also a Hyaluronidase, with Other Proteins", *The Journal of Biological Chemistry*, (1995), vol. 270, pp. 4457–4465. (GI 1362656).

Sampson, P.M. et al., "Cytokine Regulation of Human Lung Fibroblast Hyaluronan (Hyaluronic Acid) Production", *J. Clin Invest*, (1992), vol. 90, pp. 1492–1503.

Spruss, T. et al., "Hyaluronidase Significantly Enhaces the Efficacy of Regionalk Vinblastine Checmotherapy of Malignant Melanoma", *J Cancer Res Clin Oncol*, 1995, vol. 121, pp. 193–202.

Thaler, C.D., "Biochemical Characterization of a Glycosylphosphatidylinositol–Linked Hyaluronidas on Mouse Sperm", *Biochemistry*, 1995, vol. 34, pp. 7788–7795. (GI 998338).

Tu, A.T. et al., "Characterization of Lizard Venom Hyaluronidase and Evidence for its Action as a Spreading Factor", *Comp Biochem Physiol*, 1983, vol. 76, pp. 377–383.

Zhong, S.P. et al., "Biodegradation of Hyaluronic Acid Derivatives by Hyaluronidase", *Biomaterials*, 1994, vol. 15, pp. 359–365.

Zhu, X. et al., "Sequence Homology Among Sperm Antigens Involed in Mammalian Fertilization: Search for a Common Epitope for Immunocontraception", *Arch Androl*, 1994, vol. 33, pp. 141–144.

Darnell J, et al. "Molecular Biology of the Cell." Scientific American Books, Inc., NY, pp. 248–257, 1986.

*Primary Examiner*—Douglas W. Robinson
*Assistant Examiner*—Amy J. Nelson
*Attorney, Agent, or Firm*—Incyte Pharmaceuticals; Lucy J. Billings

[57] ABSTRACT

The present invention provides a polynucleotide (hhp) which identifies and encodes a novel human hyaluronidase (HHP). The invention provides for genetically engineered expression vectors and host cells comprising the nucleic acid sequence encoding HHP, and a method for making HHP with the host cells.

5 Claims, 10 Drawing Sheets

```
                 9                 18                27                36                45                54
5' ACT GGA GAG GCT CAG GCC AGG CAA GGA AGG AGG CCA CCG ACC TAC TGG GCC GAC

                63                 72                81                90                99               108
   GGA CTC CCA CAC AGT TCC TGA GCT GGT GCC AGG CAG GTG ACA CCT CCT GCA GCC

               117                126               135               144               153               162
   CCC AGC ATG CGG GCA GGC CCA GGC CCC ACC GTT ACA TTG GCC CTG GTG CTG GCG
           M   R   A   G   P   G   P   T   V   T   L   A   L   V   L   A

               171                180               189               198               207               216
   GTG KCA TGG GCC ATG GAG CTC AAG CCC ACA GCA CCA CCC ATC TTC ACT GGC CGG
   V   X   W   A   M   E   L   K   P   T   A   P   P   I   F   T   G   R

               225                234               243               252               261               270
   CCC TTT GTG GTA GCG TGG GAC GTG CCC ACA CAG GAC TGT GGC CCA CGC CTC AAG
   P   F   V   V   A   W   D   V   P   T   Q   D   C   G   P   R   L   K

               279                288               297               306               315               324
   GTG CCA CTG GAC CTG AAT GCC TTT GAT GTG CAG GCC TCA CCT AAT GAG GGT TTT
   V   P   L   D   L   N   A   F   D   V   Q   A   S   P   N   E   G   F

               333                342               351               360               369               378
   GTG AAC CAG AAT ATT ACC ATC TTC TAC CGC GAC CGT CTA GGC CTG TTA TCC ACG
   V   N   Q   N   I   T   I   F   Y   R   D   R   L   G   L   L   S   T
```

FIGURE 1A

```
        387         396         405         414         423         432
CTT CGA TTC TGC CGG AAG GTC TGT GCA TGG TGG TTG TGC CAC AGA ATG TCA GGC
L   R   F   C   R   K   V   C   A   W   W   L   C   H   R   M   S   G

        441         450         459         468         477         486
CTT TGG GCA CAC CGG AAG AAT GCT GCA GAA ACG TGT GGA GCA CTA CAT TCG GGA
L   W   A   H   R   K   N   A   A   E   T   C   G   A   L   H   S   G

        495         504         513         522         531         540
CAC ACG AGT CTG ACG GGG CTG GCG GTC ATC GAC TGG GAG GAC TGG CGA CCT GTG
H   T   S   L   T   G   L   A   V   I   D   W   E   D   W   R   P   V

        549         558         567         576         585         594
TGG GTG CGC AAC TGG CAG GAC AAA GAT GTG TAT CGC CGG TTA TCA CGC CAG CTA
W   V   R   N   W   Q   D   K   D   V   Y   R   R   L   S   R   Q   L

        603         612         621         630         639         648
GTG GCC AGT CGT CAC CCT GAC TGG CCT CCA GAC CGC ATA GTC AAA CAG GCA CAA
V   A   S   R   H   P   D   W   P   P   D   R   I   V   K   Q   A   Q

        657         666         675         684         693         702
TAT GAG TTT GAG TTC GCA GCA CAG CAG TTC ATG CTG GAG ACA CTG CGT TAT GTC
Y   E   F   E   F   A   A   Q   Q   F   M   L   E   T   L   R   Y   V

        711         720         729         738         747         756
AAG GCA GTG CGG CCC CGG CAC CTC TGG GGC TTC TAC CTC TTT CCT GAC TGC TAC
K   A   V   R   P   R   H   L   W   G   F   Y   L   F   P   D   C   Y
```

FIGURE 1B

```
        765         774         783         792         801         810
AAT CAT GAT TAT GTG CAG AAC TGG GAG AGC TAC ACA GGC CGC TGC CCT GAT GTT
N   H   D   Y   V   Q   N   W   E   S   Y   T   G   R   C   P   D   V

        819         828         837         846         855         864
GAG GTG GCC CGC AAT GAC CAG CTG GCC TGG CTG TGG GCT GAG AGC ACG GCC CTC
E   V   A   R   N   D   Q   L   A   W   L   W   A   E   S   T   A   L

        873         882         891         900         909         918
TTC CCG TCT GTC TAC CTG GAC GAG ACA CTT GCT TCC TCC CGC CAT GGC CGC AAC
F   P   S   V   Y   L   D   E   T   L   A   S   S   R   H   G   R   N

        927         936         945         954         963         972
TTT GTG AGC TTC CGT GTT CAG GAG GCC CTT CGT GTG GCT CGC ACC CAC CAT GCC
F   V   S   F   R   V   Q   E   A   L   R   V   A   R   T   H   H   A

        981         990         999        1008        1017        1026
AAC CAT GCA CTC CCA GTC TAC GTC TTC ACA CGA CCC ACC TAC AGC CGC AGG CTC
N   H   A   L   P   V   Y   V   F   T   R   P   T   Y   S   R   R   L

       1035        1044        1053        1062        1071        1080
ACG GGG CTT AGT GAG ATG GAC CTC ATC TCT ACC ATT GGC GAG AGT GCG GCC CTG
T   G   L   S   E   M   D   L   I   S   T   I   G   E   S   A   A   L

       1089        1098        1107        1116        1125        1134
GGC GCA GCT GGT GTC ATC CTC TGG GGT GAC GCG GGG TAC ACC ACA AGC ACG GAG
G   A   A   G   V   I   L   W   G   D   A   G   Y   T   T   S   T   E
```

FIGURE 1C

```
        1143        1152        1161        1170        1179        1188
ACC TGC CAG TAC CTC AAA GAT TAC CTG ACA CGG CTG CTG GTC CCC TAC GTG GTC
T   C   Q   Y   L   K   D   Y   L   T   R   L   L   V   P   Y   V   V

        1197        1206        1215        1224        1233        1242
AAT GTG TCC TGG GCC ACC CAA TAT TGC AGC CGG GCC CAG TGC CAT GGC CAT GGG
N   V   S   W   A   T   Q   Y   C   S   R   A   Q   C   H   G   H   G

        1251        1260        1269        1278        1287        1296
CGC TGT GTG CGC CGC AAC CCC AGT GCC AGT ACC TTC CTG CAT CTC AGC ACC AAC
R   C   V   R   R   N   P   S   A   S   T   F   L   H   L   S   T   N

        1305        1314        1323        1332        1341        1350
AGT TTC CGC CTA GTG CCT GGC CAT GCA CCT GGT GAA CCC CAG CTG CGA CCT GTG
S   F   R   L   V   P   G   H   A   P   G   E   P   Q   L   R   P   V

        1359        1368        1377        1386        1395        1404
GGG GAG CTC AGT TGG GCC GAC ATT GAC CAC CTG CAG ACA CAC TTC CGC TGC CAG
G   E   L   S   W   A   D   I   D   H   L   Q   T   H   F   R   C   Q

        1413        1422        1431        1440        1449
TGT ACT TTG GCT TGA GTG GTT AGC AAT GCC AAT NGG ACC ATA GGC A 3'
C   T   L   A
```

FIGURE 1D

The Electronic Northern for Clone: 705483
and Stringency = 50

| Library | Lib Description | Abun | Pct Abun |
|---|---|---|---|
| LUNGNOT02 | lung, 47 M | 4 | 0.098 |
| THYRNOT02 | thyroid, hyperthyroidism, 16 F | 2 | 0.060 |
| LATRTUT02 | heart tumor, myoma, 43 M | 2 | 0.055 |
| BRAITUT01 | brain tumor, oligoastrocytoma, 50 F | 4 | 0.054 |
| HUVENOB01 | HUVEC endothelial cell line, control | 1 | 0.042 |
| THP1PLB02 | THP-1 promonocyte cell line, treated PMA, LPS | 1 | 0.041 |
| LUNGNOT03 | lung, 79 M, match to LUNGTUT02 | 2 | 0.040 |
| BRAINOT04 | brain, hemorrhage, 44 M | 1 | 0.036 |
| SYNORAT04 | synovium, wrist, rheumatoid, 62 F | 2 | 0.035 |
| BRAITUT02 | brain tumor, metastasis, 58 M | 2 | 0.034 |
| NGANNOT01 | ganglioneuroma, 9 M | 2 | 0.031 |
| COLNNOT05 | colon, 40 M, match to COLNCRT01 | 1 | 0.029 |
| LUNGNOT09 | lung, fetal M | 1 | 0.029 |
| TESTTUT02 | testicular tumor, 31 M | 1 | 0.028 |
| BRSTNOM02 | breast, F, NORM, WM | 1 | 0.021 |
| LUNGAST01 | lung, asthma, 17 M | 1 | 0.015 |
| BRSTNOT03 | breast, 54 F, match to BRSTTUT02 | 1 | 0.015 |
| PANCNOT05 | pancreas, 2 M | 1 | 0.015 |
| PLACNOM02 | placenta, neonatal F, NORM, WM | 2 | 0.011 |
| BRAINOM01 | brain, infant F, NORM, WM | 2 | 0.009 |
| LIVSFEM02 | liver/spleen, fetal M, NORM, WM | 2 | 0.006 |

FIGURE 2

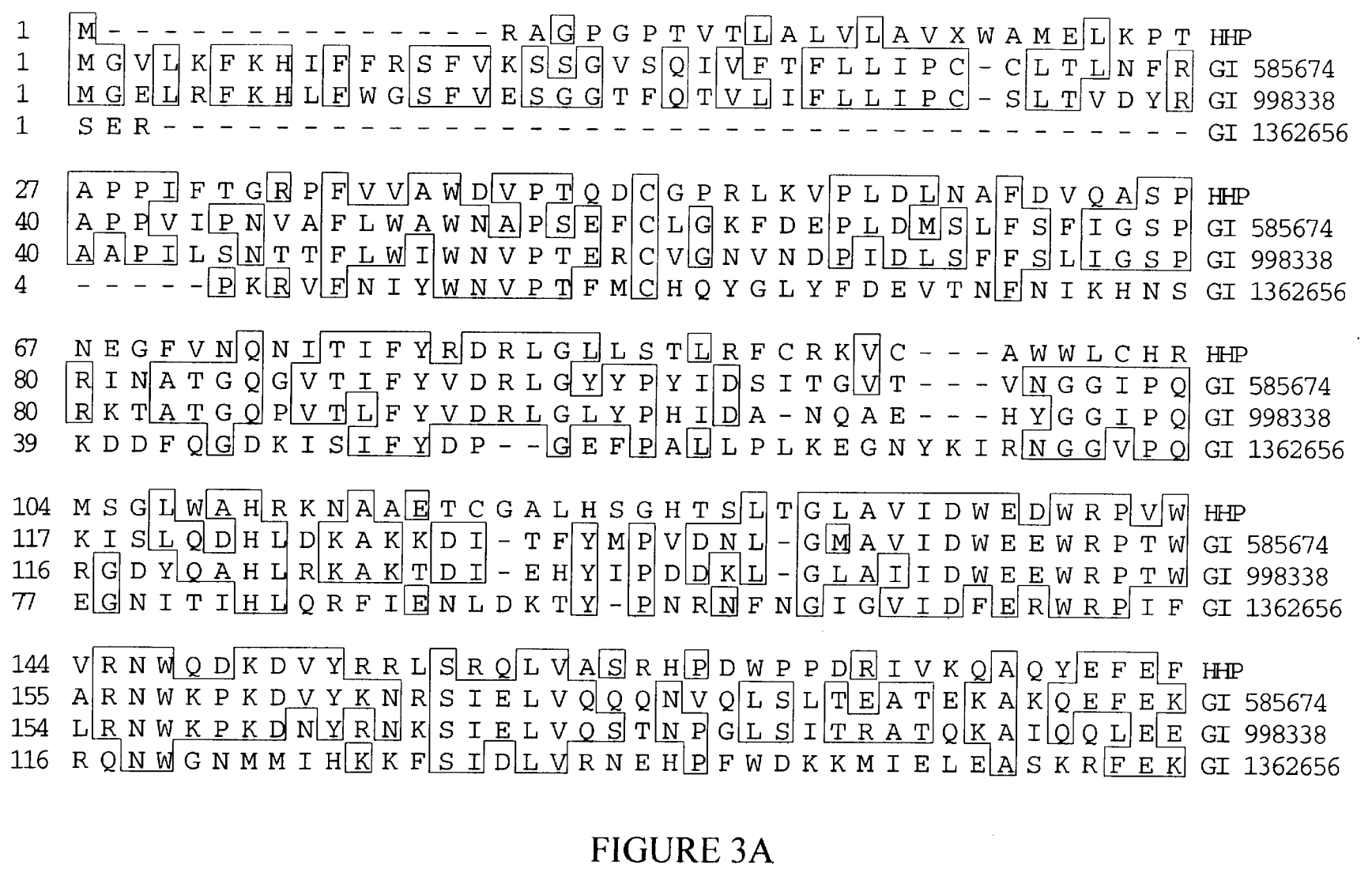

```
1    M - - - - - - - - - - - - - - R A G P G P T V T L A L V L A V X W A M E L K P T   HHP
1    M G V L K F K H I F F R S F V K S S G V S Q I V F T F L L I P C - C L T L N F R   GI 585674
1    M G E L R F K H L F W G S F V E S G G T F Q T V L I F L L I P C - S L T V D Y R   GI 998338
1    S E R - - - - - - - - - - - - - - - - - - - - - - - - - - - - - - - - - - - - -   GI 1362656

27   A P P I F T G R P F V V A W D V P T Q D C G P R L K V P L D L N A F D V Q A S P   HHP
40   A P P V I P N V A F L W A W N A P S E F C L G K F D E P L D M S L F S F I G S P   GI 585674
40   A A P I L S N T T F L W I W N V P T E R C V G N V N D P I D L S F F S L I G S P   GI 998338
4    - - - - - P K R V F N I Y W N V P T F M C H Q Y G L Y F D E V T N F N I K H N S   GI 1362656

67   N E G F V N Q N I T I F Y R D R L G L L S T L R F C R K V C - - - A W W L C H R   HHP
80   R I N A T G Q G V T I F Y V D R L G Y Y P Y I D S I T G V T - - - V N G G I P Q   GI 585674
80   R K T A T G Q P V T L F Y V D R L G L Y P H I D A - N Q A E - - - H Y G G I P Q   GI 998338
39   K D D F Q G D K I S I F Y D P - - G E F P A L L P L K E G N Y K I R N G G V P Q   GI 1362656

104  M S G L W A H R K N A A E T C G A L H S G H T S L T G L A V I D W E D W R P V W   HHP
117  K I S L Q D H L D K A K K D I - T F Y M P V D N L - G M A V I D W E E W R P T W   GI 585674
116  R G D Y Q A H L R K A K T D I - E H Y I P D D K L - G L A I I D W E E W R P T W   GI 998338
77   E G N I T I H L Q R F I E N L D K T Y - P N R N F N G I G V I D F E R W R P I F   GI 1362656

144  V R N W Q D K D V Y R R L S R Q L V A S R H P D W P P D R I V K Q A Q Y E F E F   HHP
155  A R N W K P K D V Y K N R S I E L V Q Q Q N V Q L S L T E A T E K A K Q E F E K   GI 585674
154  L R N W K P K D N Y R N K S I E L V Q S T N P G L S I T R A T Q K A I Q Q L E E   GI 998338
116  R Q N W G N M M I H K K F S I D L V R N E H P F W D K K M I E L E A S K R F E K   GI 1362656
```

FIGURE 3A

```
184 A A Q Q F M L E T L R Y V K A V R P R H L W G F Y L F P D C Y N H D Y V Q N W E HHP
195 A G K D F L V E T I K L G K L L R P N H L W G Y Y L F P D C Y N H H Y K K P - - GI 585674
194 A G R K F M E G T L H L G K F L R P N Q L W G Y Y L F P D C Y N N K F Q D P - - GI 998338
156 Y A R L F M E E T L K L A K K T R K Q A D W G Y Y G Y P Y C F N - - - M S P - N GI 1362656

224 S Y T G R C P D V E V A R N D Q L A W L W A E S T A L F P S V Y L D E T L A S S HHP
233 G Y N G S C F N V E I K R N D D L S W L W N E S T A L Y P S I Y L N T Q - Q S P GI 585674
232 K Y D G Q C P A V E K K R N D N L K W L W K A S T G L Y P S V Y L K K D L K S N GI 998338
192 N L V P D C D A T A M L E N D K M S W L F N N Q N V L L P S V Y I R H E L T P D GI 1362656

264 R H G R N F V S F R V Q E A L R V A R T H H A N H A L P V Y V F T R P T Y S R R HHP
272 V A A T L Y V R N R V R E A I R V S K I P D A K S P L P V F A Y T R I V F T D Q GI 585674
272 R Q A T L Y V R Y R V V E A I R V S K V G N A S D P V P I F V Y I R L V F T D R GI 998338
232 Q R V G L - V Q G R V K E A V R I S - - N N L K H S P K V L S Y W W Y V Y Q D D GI 1362656

304 L T G - L S E M D L I S T I G E S A A L G A A G V I L W G D A G Y T T S T E T C HHP
312 V L K F L S Q D E L V Y T F G E T V A L G A S G I V I W G T L S I M R S M K S C GI 585674
312 T S E Y L L E D D L V N T I G E I V A L G T S G I I I W D A M S L A Q R A A G C GI 998338
269 T N T F L T E T D V K K T F Q E I A I N G G D G I I I W G S S S D V N S L S K C GI 1362656

343 Q Y L K D Y L T R L L V P Y V V N V S W A T Q Y C S R A Q C H G H G R C V R R N HHP
352 L L L D N Y M E T I L N P Y I I N V T L A A K M C S Q V L C Q E Q G V C I R K N GI 585674
352 P I L H K Y M Q T T L N P Y I V N V T L A A K M C S Q T L C N E K G M C S R R K GI 998338
309 K R L R E Y L L T V L G P I T V N V T - - - - - - - - - - - - - - - - - - - - - GI 1362656
```

FIGURE 3B

```
383 P S A S T F L H L S T N S F R L V P G H A P G E P Q L R P V G E L S W A D I D H HHP
392 W N S S D Y L H L N P D N F A I Q L E K G - - - G K F T V R G K P T L E D L E Q GI 585674
392 E S S D V Y L H L N P S H F D I M L T E T - - - G K Y E V L G N P R V G D L E Y GI 998338
328 - - - - - - - - - - - - - - - - - - - - - - - - - - - - - - - - - - - - - - - - GI 1362656

423 L Q T H F R C Q C - - - - - - - - - - - - - - - - - - - - - - - - - - - - - - - HHP
429 F S E K F Y C S C Y S T L S C K E K A D V K D T D A V D V C I A D G V C I D A F GI 585674
429 F S E H F K C S C F S R M T C K E T S D V K N V Q D V N V C V G D N V C I K A K GI 998338
328 - - - - - - - - - - - - - - - - - - - - - - - - - - - - - - - - - - - - E T V N GI 1362656

432 - - - - - - - - - - - - - - - - - - - - - - - - T L A HHP
469 L K P P M E T E E P Q I F Y N A S P S - - - - - T L S A T M F I V S I L F L I I GI 585674
469 V E P - - - - - N P A F Y L L P G K S L L F M T T L G H V L Y H L P Q D I F V F GI 998338
331 GI 1362656

434 HHP
504 S S - - - V A S L GI 585674
504 P R K T L V S T P GI 998338
331 GI 1362656
```

FIGURE 3C

HUMAN HYALURONIDASE

FIELD OF THE INVENTION

The present invention relates to nucleic acid and amino acid sequences of a novel human hyaluronidase and to the use of these sequences in the diagnosis, study, prevention and treatment of disease.

BACKGROUND OF THE INVENTION

A typical mammalian egg is surrounded by an outer layer of about 3,000 cumulus cells embedded in an extracellular matrix rich in the high molecular mass polysaccharide hyaluronic acid (HA). The sperm protein PH-20 has hyaluronidase activity and is present on the plasma membrane of mouse and human sperm (Lin Y et al (1994) J Cell Biol 125: 1157–63). PH-20 enables sperm to penetrate the egg's cumulus barrier, an essential step in the fertilization process. Biochemical characterization of PH-20 revealed the existence of both a soluble isoform and a glycosylphosphotidylinositol (GPI) linked isoform, in which PH-20 is bound to the membrane of the sperm acrosome (Thaler CD et al (1995) Biochemistry 34: 7788–7795). Sequence analysis indicates a GPI-anchor attachment site at amino acid position number 490 (Lin et al, supra).

HA acts in processes other than fertilization. It is a found in the extracellular matrix of many cells, especially in soft connective tissues. HA has been assigned various physiological functions, such as in water and plasma protein homeostasis (Laurent TC et al (1992) FASEB J 6: 2397–2404). HA production increases in proliferating cells and may play a role in mitosis. It has also been implicated in locomotion and cell migration. HA seems to play important roles in cell regulation, development, and differentiation (Laurent et al, supra).

There is evidence for the expression of one or more non-testicular hyaluronidases. Evidence suggests that fibroblast HA degradation in the lung is mediated by a previously unrecognized lysosomal-type hyaluronidase whose activity is regulated by various cytokines (Sampson PM et al (1992) J Clin Invest 90: 1492–1503).

The venom of numerous animals including various snakes, bees, hornets, stone fish, platypus, scorpions, and lizards contain hyaluronidase. Hyaluronidase from the white face hornet is an allergen which induces an IgE response in susceptible people (Lu G et al (1995) J Biol Chem 270: 4457–4465). Venom hyaluronidase is thought to act as a "spreading factor", an aid in the diffusion of toxins. Researchers have found that lizard venom hyaluronidase promotes the spread of the hemorrhagic area in mice injected with hemorrhagic toxin (Tu AT et al (1983) Comp Biochem Physiol 76: 377–383).

Clinical Applications of Hyaluronidases

Effective contraception (100%) was obtained in male and female guinea pigs immunized with PH-20 (Primakoff P et al (1988) Nature 335: 543–546). Based on these results researchers are continuing efforts to make an anti-sperm PH-20 contraceptive vaccine suitable for humans (Zhu X et al (1994) Arch Androl 33: 141–144).

HA has been chemically modified as a biomaterial for medical applications such as controlled drug release matrices, nerve guides, and wound dressings (Zhong SP et al (1994) Biomaterials 15: 359–365). These materials are being tested for their stability in cellular environments in which naturally occurring hyaluronidase is present.

HA has been used in clinical medicine. Its tissue protective and Theological properties have proved useful in ophthalmic surgery. Serum HA is diagnostic of liver disease and various inflammatory conditions, such as rheumatoid arthritis. Interstitial edema caused by accumulation of HA may cause disfunction in various organs (Laurent et al, supra).

HA is known to produce tumor cell adhesion and migration, and its small fragments are angiogenic. Lokeshwar VB et al (1996; Cancer Res 56: 651–657)reported a significant elevation of hyaluronidase activity in prostate tumor tissue compared to that in both normal prostate and benign prostate hyperplasia. Furthermore, hyaluronidase levels in tissues correlate well with tumor progression.

Clinical trials have shown that the combined therapy of vindesine, cisplatin, hyaluronidase, and radiation is well tolerated by most patients and highly effective against advanced squamous cell cancer of the head and neck (Klocker J et al (1995) Am J Clin Oncol 18: 425–428). In preclinical experiments the combination of hyaluronidase and the chemotherapeutic drug vinblastine had significant antitumor effects on SK-Mel-3 melanoma cells implanted in nude mice (Spruss T et al (1995) J Cancer Res Clin Oncol 121: 193–202). Furthermore, hyaluronidase was well tolerated in test animals and prevented the local inflammation reactions that are commonly seen after subcutaneous vinblastine injections.

As shown above, there are numerous clinical applications for known hyaluronidases and the existence of at least one additional human hyaluronidases has been inferred. The selective modulation of expression and activity of a novel hyaluronidase may allow successful management of diseases associated with HA, such as cancer and inflammatory conditions.

SUMMARY OF THE INVENTION

The present invention discloses a novel hyaluronidase, HHP, characterized as having homology to the PH-20 hyaluronidases. Accordingly, the invention features a substantially purified hyaluronidase, as shown in amino acid sequence of SEQ ID NO:1, and having characteristics of the PH-20 family of hyaluronidases.

One aspect of the invention features isolated and substantially purified polynucleotides which encode HHP. In a particular aspect, the polynucleotide is the nucleotide sequence of SEQ ID NO:2. In addition, the invention features polynucleotide sequences that hybridize under stringent conditions to SEQ ID NO:2.

A nucleic acid sequence encoding HHP, oligonucleotides, peptide nucleic acids (PNA), fragments, portions or antisense molecules thereof, may be used in diagnostic assays of body fluids or biopsied tissues to detect the expression level of a nucleic acid sequence encoding HHP. For example, a nucleic acid sequence encoding HHP designed from SEQ ID NO:2 can be used to detect the presence of the mRNA transcripts in a patient or to monitor modulation of the transcripts during treatment.

The present invention relates, in part, to the inclusion of the polynucleotide encoding HHP in an expression vector which can be used to transform host cells or organisms. Such transgenic hosts are useful for the production of HHP. Substantially purified HHP or fragments thereof may be useful as a pharmaceutical composition. For example, they may be used to inhibit or reverse the development of tumors.

A nucleic acid sequence encoding HHP also provides for the design of antisense molecules useful in diminishing or eliminating expression of the genomic nucleotide sequence in conditions where HHP activity may hinder a desired HA activity.

The invention further provides diagnostic assays and kits for the detection of naturally occurring HHP. It provides for the use of substantially purified HHP as a positive control and to produce anti-HHP antibodies which can be used to quantitate the amount of HHP in human body fluids or biopsied tissues. HHP can also be used to identify agonists which induce the production of or prolong the lifespan of the HHP molecule in vivo or in vitro.

The invention also relates to pharmaceutical compositions comprising HHP, antisense molecules capable of disrupting expression of the genomic sequence encoding HHP, and agonists, antibodies, antagonists or inhibitors of the HHP. These compositions are useful for the prevention or treatment of conditions associated with the presence of HA or the expression of HHP.

BRIEF DESCRIPTION OF THE FIGURES

FIGS. 1A, 1B, 1C, and 1D show the nucleic acid sequence (SEQ ID NO:2) and deduced amino acid sequence (SEQ ID NO:1) of the human PH-20 homolog, HHP and was produced using MacDNAsis software (Hitachi Software Engineering Co Ltd).

FIG. 2 shows the northern analysis for Incyte Clone 705483 (SEQ ID NO:2) produced electronically using LIFESEQ™ database (Incyte Pharmaceuticals, Palo Alto CA). The percentage abundance is defined as 100 times the number of transcripts of the nucleic acid encoding HHP found in the library divided by the total number of transcripts in the library.

FIGS. 3A, 3B, and 3C show the amino acid sequence alignments among HHP (SEQ ID NO:1), human PH-20 (GI 585674; SEQ ID NO:3), mouse PH-20 (GI 998338; SEQ ID NO:4), and hornet hyaluronoglucuronidase (GI 1362656; SEQ ID NO: 5) produced using the multisequence alignment program of DNAStar software (DNAStar Inc, Madison WI).

DETAILED DESCRIPTION OF THE INVENTION

DEFINITIONS

Figure 4:
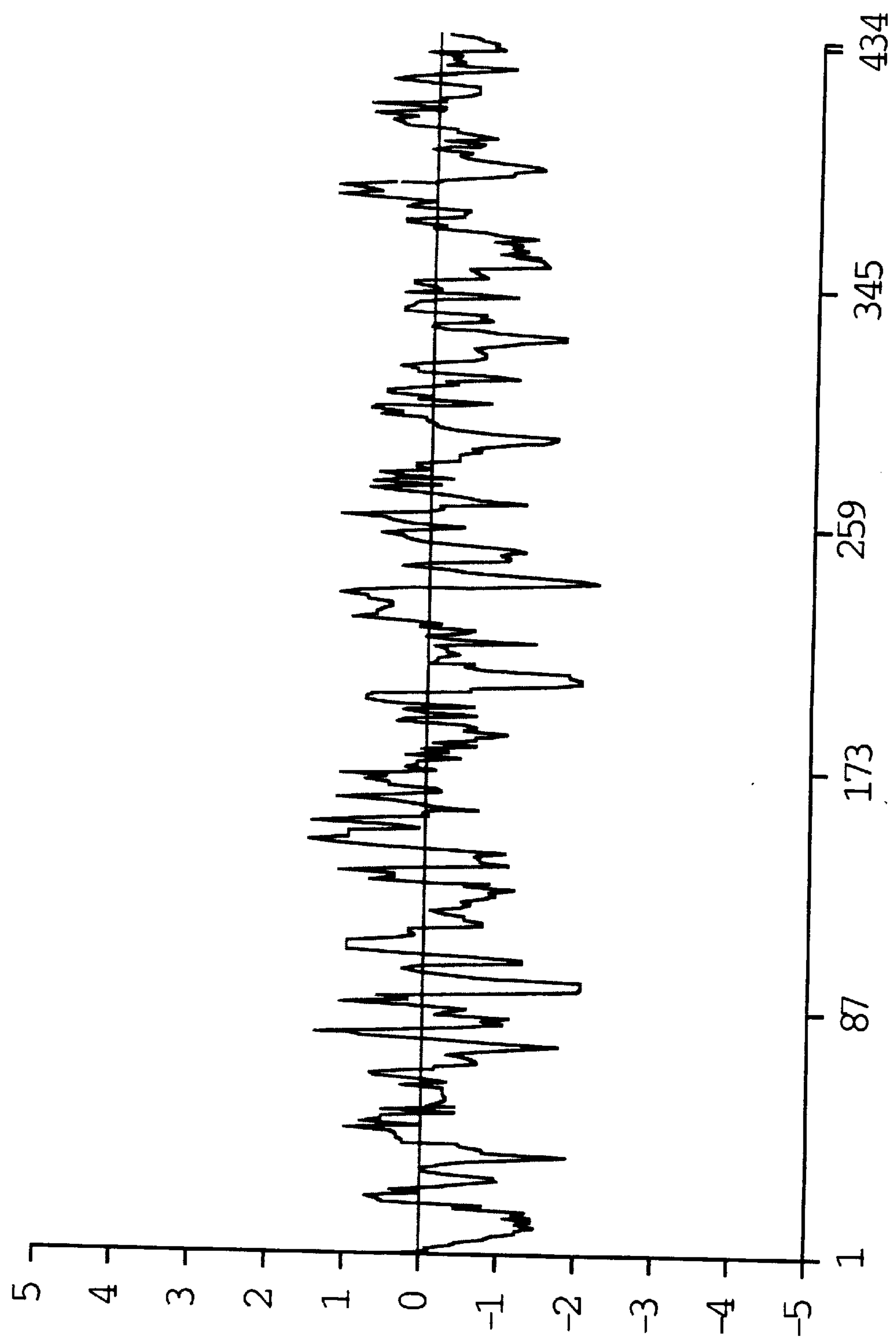
FIG. 4 shows the hydrophobicity plot (generated using MacDNAsis software) for HHP, SEQ ID NO:1; the X axis reflects amino acid position, and the negative Y axis, hydrophobicity (FIGS. 4 and 5).

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to protein or peptide sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen PE et al (1993) Anticancer Drug Des 8:53–63).

As used herein, HHP refers to the amino acid sequence of substantially purified HHP obtained from any species, particularly mammalian, including bovine, ovine, porcine, murine, equine, and preferably human, from any source whether natural, synthetic, semi-synthetic or recombinant.

The present invention also encompasses HHP variants. A preferred HHP variant is one having at least 80% amino acid sequence similarity to the HHP amino acid sequence (SEQ ID NO:1), a more preferred HHP variant is one having at least 90% amino acid sequence similarity to SEQ ID NO:1 and a most preferred HHP variant is one having at least 95% amino acid sequence similarity to SEQ ID NO:1.

A "variant" of HHP may have an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to a HHP having structural, regulatory or biochemical functions of the naturally occurring HHP. Likewise, "immunologically active" defines the capability of the natural, recombinant or synthetic HHP, or any oligopeptide thereof, to induce a specific immune response in appropriate animals or cells and to bind with specific antibodies.

The term "derivative" as used herein refers to the chemical modification of a nucleic acid sequence encoding HHP or the encoded HHP. Illustrative of such modifications would be replacement of hydrogen by an alkyl, acyl, or amino group. A nucleic acid derivative would encode a polypeptide which retains essential biological characteristics of natural HHP.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

The present invention relates to a novel human PH-20 homolog, HHP, initially identified among the partial cDNAs from a rheumatoid knee synovium library (SYNORAT04) and to the use of the nucleic acid and amino acid sequences disclosed herein in the study, diagnosis, prevention and treatment of disease. Nucleic acid encoding a portion of HHP was also found in cDNA libraries in tissues from lung, umbilical cord endothelium, various tumors, and inflamed tissues from the thyroid, brain, joint synovium, and lung (FIG. 2).

Figure 5:
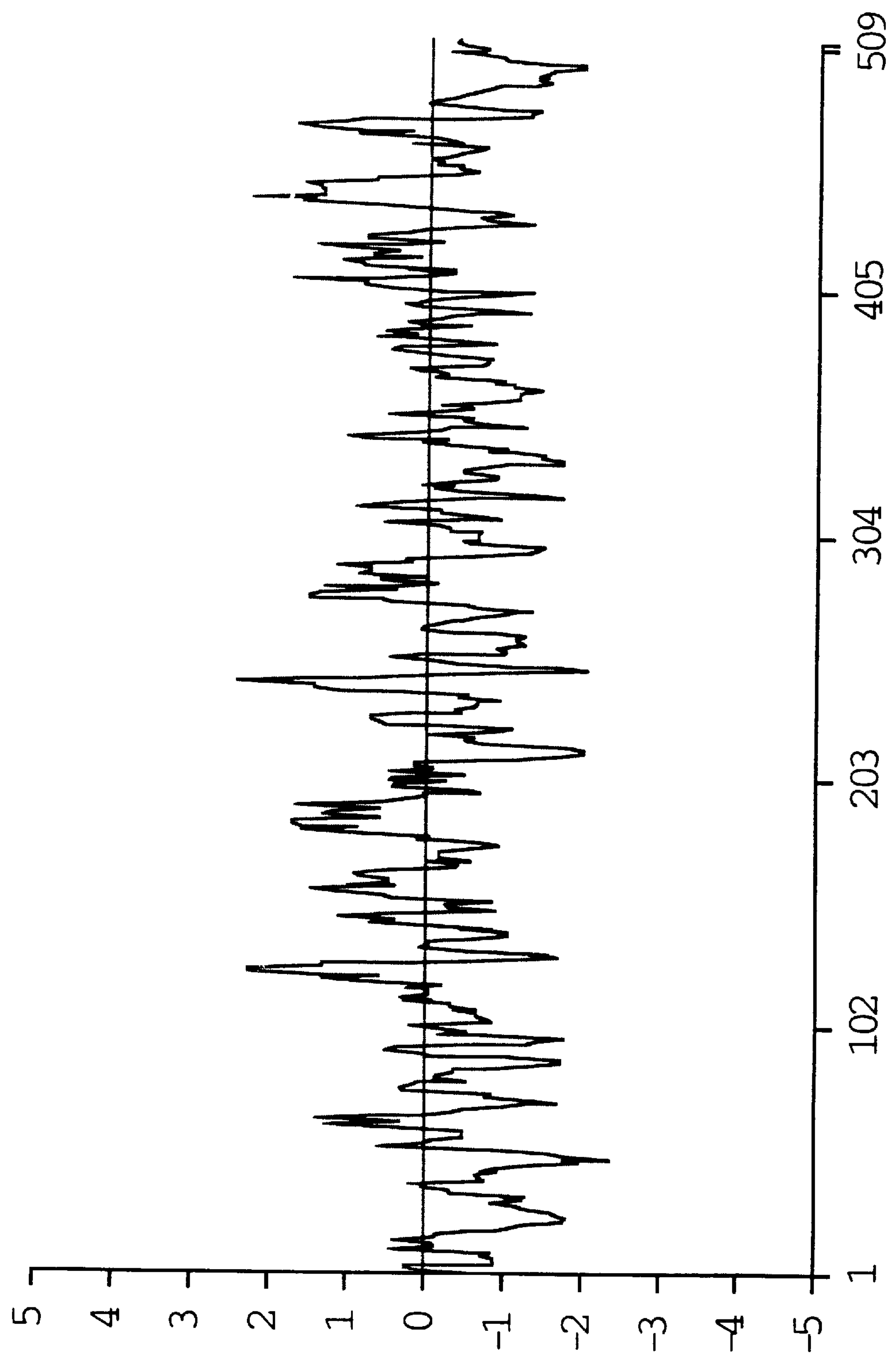
FIG. 5 shows the hydrophobicity plot for human PH-20, SEQ ID NO:3.

Nucleic acid encoding a portion of HHP was first identified in the cDNA, Incyte Clone 705483 (SEQ ID NO:2), through a computer-generated search for amino acid sequence alignments. The nucleic acid sequence, SEQ ID NO:2; disclosed herein and designated in lower case (hhp) encodes the amino acid sequence, SEQ ID NO:1, disclosed hereinafter as HHP. The present invention is based, in part, on the chemical and structural homology among HHP, human PH-20 (GI 585674; Lin Y et al (1993), Proc Natl Acad Sci USA 90: 10071–5), mouse PH-20 (GI 998338; Thaler CD et al (1995) Biochemistry 34: 7788–7795), and hornet hyaluronoglucuronidase (GI 1362656; Lu G et al (1995) J Biol Chem 270: 4457–4465; FIGS. 3A and 3B). HHP has 36% identity in amino acid sequence to human PH-20. HHP does not have homology to the carboxy-terminal 67 amino acids of PH-20 and lacks a putative GPI-binding site. As illustrated by FIGS. 4 and 5, HHP and GI 585674 have similar hydrophobicity plots suggesting shared configuration and activity. HHP is 434 amino acids long and has three potential glycosylation sites.

The HHP Coding Sequences

The nucleic acid and deduced amino acid sequences of HHP are shown in FIGS. 1A, 1B, 1C, and 1D. In accordance with the invention, any nucleic acid sequence which encodes the amino acid sequence of HHP can be used to generate recombinant molecules which express HHP. In a specific embodiment described herein, a partial sequence of hhp was first isolated as Incyte Clone 705483 from a rheumatoid knee synovium cDNA library (SYNORAT04), disclosed in U.S. Pat. application Ser. No.60/009,132 entitled "Polynucleotides and Polypeptides Derived from Rheumatoid Synovium" by Stuart et al and filed Dec. 22, 1995, the disclosure of which is incorporated herein by reference.

It will be appreciated by those skilled in the art that as a result of the degeneracy of the genetic code, a multitude of HHP-encoding nucleotide sequences, some bearing minimal homology to the nucleotide sequences of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring HHP, and all such variations are to be considered as being specifically disclosed.

Although nucleotide sequences which encode HHP and its variants are preferably capable of hybridizing to the nucleotide sequence of the naturally occurring hhp under appropriately selected conditions of stringency, it may be advantageous to produce nucleotide sequences encoding HHP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HHP and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a HHP and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a hhp sequence or any portion thereof.

Also included within the scope of the present invention are polynucleotide sequences that are capable of hybridizing to the nucleotide sequence of FIGS. 1A, 1B, 1C, and 1D under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and confer may be used at a defined "stringency" as explained below.

"Maximum stringency" typically occurs at about Tm−5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification as carried out in the polymerase chain reaction technologies described in Dieffenbach CW and GS Dveksler (1995, *PCR Primer, a Laboratory Manual*, Cold Spring Harbor Press, Plainview N.Y.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring hhp or HHP.

A "substitution" results from the replacement of one or more nucleotides or amino acids by different nucleotides or amino acids, respectively.

Altered hhp nucleic acid sequences which may be used in accordance with the invention include deletions, insertions or substitutions of different nucleotides resulting in a polynucleotide that encodes the same or a functionally equivalent HHP. The protein may also show deletions, insertions or substitutions of amino acid residues which produce a silent change and result in a functionally equivalent HHP. Deliberate amino acid substitutions may be made on the basis of similarity in polarity, charge, solubility, hydrophobicity, hydrophilicity, and/or the amphipathic nature of the residues as long as the biological activity of HHP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of hhp. As used herein, an "allele" or "allelic sequence" is an alternative form of hhp. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, Sequenase® (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown MA) and the ABI 377 DNA sequencers (Perkin Elmer).

Extending the Polynucleotide Sequence

The polynucleotide sequence of hhp may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Parker J D et al (1991; Nucleic Acids Res 19:3055–60), teach walking PCR, a method for targeted gene walking which permits retrieval of unknown sequence. PromoterFinder™ a new kit available from Clontech (Palo Alto Calif.) uses PCR, nested primers and PromoterFinder libraries to walk in genomic DNA. This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez MC et al (1993) Anal Chem 65:2851–8).

Expression of the Nucleotide Sequence

In accordance with the present invention, polynucleotide sequences which encode HHP, fragments of the polypeptide, fusion proteins or functional equivalents thereof may be used in recombinant DNA molecules that direct the expression of HHP in appropriate host cells. Due to the inherent degeneracy of the genetic code, other DNA sequences which encode substantially the same or a functionally equivalent amino acid sequence, may be used to clone and express HHP. As will be understood by those of skill in the art, it may be advantageous to produce HHP-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of HHP expression or to produce recombinant RNA transcripts having desirable properties, such as a longer half-life, than transcripts produced from naturally occurring sequence.

The nucleotide sequences of the present invention can be engineered in order to alter a hhp coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant hhp sequence may be ligated to a heterologous sequence to encode a fusion protein. For example, for screening of peptide libraries for inhibitors of HHP activity, it may be useful to encode a chimeric HHP protein that is recognized by a commercially available antibody. A fusion protein may also be engineered to contain a cleavage site located between a HHP sequence and the heterologous protein sequence, so that the HHP may be cleaved and substantially purified away from the heterologous moiety.

In an alternate embodiment of the invention, the coding sequence of hhp could be synthesized, whole or in part, using chemical methods well known in the art (see Caruthers MH et al (1980) Nuc Acids Res Symp Ser 215–23, Horn T et al(1980) Nuc Acids Res Symp Ser 225–32, etc). Alternatively, the protein itself could be produced using chemical methods to synthesize a HHP amino acid sequence, whole or in part. For example, peptide synthesis can be performed using various solid-phase techniques (Roberge JY et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles*, WH Freeman and Co, New York N.Y.). The composition of the synthetic peptides may be confirmed by amino acid analysis or sequencing (eg, the Edman degradation procedure; Creighton, supra). Additionally the amino acid sequence of HHP, or any part thereof, may be altered during direct synthesis and/or combined using chemical methods with sequences from other proteins, or any part thereof, to produce a variant polypeptide.

Expression Systems

In order to express a biologically active HHP, the nucleotide sequence encoding HHP or its functional equivalent, is inserted into an appropriate expression vector, ie, a vector which contains the necessary elements for the transcription and translation of the inserted coding sequence.

Methods which are well known to those skilled in the art can be used to construct expression vectors containing a HHP coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F M et al (1989) *Current Protocols in Molecular Biology*, John Wiley & Sons, New York N.Y.

A variety of expression vector/host systems may be utilized to contain and express a hhp coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacz promoter of the Bluescript® phagemid (Stratagene, LaJolla Calif.) or psportl (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of hhp, vectors based on SV40 or EBV may be used with an appropriate selectable marker.

In bacterial systems, a number of expression vectors may be selected depending upon the use intended for HHP. For example, when large quantities of HHP are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the hhp coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. PGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding HHP may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi RM (1991) Results Probl Cell Differ 17:85–105) may be used. These constructs can be introduced into plant cells by direct DNA transformation or pathogen-mediated transfection. For reviews of such techniques, see Hobbs S or Murry LE in McGraw Hill *Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which could be used to express HHP is an insect system. In one such system, *Autographa californica* nuclear polyhedrosis virus (AcNPV) is used as a vector to express foreign genes in *Spodoptera frugiperda* cells or in *Trichoplusia* larvae. The hhp coding sequence may be cloned into a nonessential region of the virus, such as the polyhedrin gene, and placed under control of the polyhedrin promoter. Successful insertion of hhp will render the polyhedrin gene inactive and produce recombinant virus lacking coat protein coat. The recombinant viruses are then used to infect *S. frugiperda* cells or *Trichoplusia* larvae in which HHP is expressed (Smith et al (1983) J Virol 46:584; Engelhard EK et al (1994) Proc Nat Acad Sci 91:3224–7).

In mammalian host cells, a number of viral-based expression systems may be utilized. In cases where an adenovirus is used as an expression vector, a hhp coding sequence may be ligated into an adenovirus transcription/translation complex consisting of the late promoter and tripartite leader sequence. Insertion in a nonessential E1 or E3 region of the viral genome will result in a viable virus capable of expressing HHP in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a hhp sequence. These signals include the ATG initiation codon and adjacent sequences. In cases where hhp, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express hhp may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman SC and RC Mulligan (1988) Proc NatI Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes CA et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the hhp is inserted within a marker gene sequence, recombinant cells containing hhp can be identified by the absence of marker gene function. Alternatively, a marker gene can be placed in tandem with a HHP sequence under the control of a single promoter. Expression of the marker gene in response to induction or selection usually indicates expression of the tandem hhp as well.

Alternatively, host cells which contain the coding sequence for hhp and express HHP may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the hhp polynucleotide sequence can be detected by DNA-DNA or DNA-RNA hybridization or amplification using probes, portions or fragments of hhp. Nucleic acid amplification based assays involve the use of oligonucleotides or oligomers based on the hhp sequence to detect transformants containing hhp DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of HHP, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HHP is preferred, but a competitive binding assay may be employed. These and other assays are described, among other places, in Hampton R et al (1990*, Serological Methods, a Laboratory Manual*, APS Press, St Paul Minn.) and Maddox DE et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to hhp include oligolabeling, nick translation, end-labeling or PCR amplification using a labeled nucleotide. Alternatively, the hhp sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of HHP

Host cells transformed with a hhp nucleotide sequence may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing hhp can be designed with signal sequences which direct secretion of HHP through a prokaryotic or eukaryotic cell membrane. Other recombinant constructions may join hhp to nucleotide sequence encoding a polypeptide domain which will facilitate purification of soluble proteins (Kroll DJ et al (1993) DNA Cell Biol 12:441–53; of discussion of vectors infra containing fusion proteins).

HHP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and HHP is useful to facilitate purification. One such expression vector provides for expression of a fusion protein compromising an HHP and contains nucleic acid encoding 6 histidine residues followed by thioredoxin and an enterokinase cleavage site. The histidine residues facilitate purification on IMIAC (immobilized metal ion affinity chromotography as described in Porath et al (1992) Protein Expression and Purification 3: 263–281) while the enterokinase cleavage site provides a means for purifying the chemokine from the fusion protein.

In addition to recombinant production, fragments of HHP may be produced by direct peptide synthesis using solid-phase techniques (cf Stewart et al (1969) *Solid-Phase Peptide Synthesis*, WH Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of HHP may be chemically synthesized separately and combined using chemical methods to produce the full length molecule.

Uses of HHP

The rationale for use of the nucleotide and polypeptide sequences disclosed herein is based in part on the chemical and structural homology between the novel human HHP and human PH-20 (GI 585674; Lin et al, supra).

Lin et al (1994; supra) found the PH-20 enables sperm to penetrate the cumulus cell layer surrounding the egg. A similar hyaluronidase activity in HHP may be useful for artificially inducing fertilization in vitro by proving additional enzyme to assist in the breaking down of the HA that surrounds mammalian eggs.

Tu et al (1983; supra) found that hyaluronidase promotes the spread of hemorrhagic area due to lizard venom. Agents that block HHP may also block hyaluronidase from the many sources of venom in which it occurs.

HA has been chemically modified as a biomaterial for medical applications such as controlled drug release matrices, nerve guides, and wound dressings (Zhong SP et al (1994) Biomaterials 15: 359–365). These materials are being tested as to their stability in cellular environments in which hyaluronidase is present. HA derived biomaterials may be directly tested for stability in the presence of HHP.

Spruss et al (1995; supra) found that hyaluronidase significantly enhances the efficacy of regional vinblastine chemotherapy of malignant melanoma. Klocker et al (1995; supra) found that the combined therapy of vindesine, cisplatin, hyaluronidase, and radiation is well tolerated by most patients and highly effective against advanced squamous cell cancer of the head and neck. HHP may be similarly applied in chemotherapeutic regimens for melanomas, head and neck cancers, or other cancers.

Laurent et al (1992; supra) suggested that interstitial edema resulting in disfunction in various organs may be caused by accumulation of HA. HHP may decrease levels of HA and lessen the harm brought on by edema.

In disorders or conditions where HA is desirable, cells could be transfected with antisense sequences of hhp or provided with inhibitors of HHP so as to lessen the undesired breakdown of HA.

HHP Antibodies

HHP-specific antibodies are useful for the diagnosis of conditions and diseases associated with expression of HHP. HHP for antibody induction does not require biological activity; however, the protein fragment, or oligopeptide must be antigenic. Peptides used to induce specific antibodies may have an amino acid sequence consisting of at least five amino acids, preferably at least 10 amino acids. They should mimic a portion of the amino acid sequence of the natural protein and may contain the entire amino acid sequence of a small, naturally occurring molecule. Short stretches of HHP amino acids may be fused with those of another protein such as keyhole limpet hemocyanin and antibody produced against the chimeric molecule. Procedures well known in the art can be used for the production of antibodies to HHP Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

For the production of antibodies, various hosts including goats, rabbits, rats, mice, etc may be immunized by injection with HHP or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to HHP may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce HHP-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for HHP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between HHP and its specific antibody and the measurement of complex formation. A two-site, monoclonal-based immunoassay utilizing monoclonal antibodies reactive to two noninterfering epitopes on a specific HHP protein is preferred, but a competitive binding assay may also be employed. These assays are described in Maddox DE et al (1983, J Exp Med 158:1211).

Diagnostic Assays Using HHP Specific Antibodies

Particular HHP antibodies are useful for the diagnosis of conditions or diseases characterized by expression of HHP or in assays to monitor patients being treated with HHP, agonists or inhibitors. Diagnostic assays for HHP include methods utilizing the antibody and a label to detect HHP in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring HHP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HHP is preferred, but a competitive binding assay may be employed. These assays are described, among other places, in Maddox, Del. et al (1983, J Exp Med 158:1211).

In order to provide a basis for diagnosis, normal or standard values for HHP expression must be established. This is accomplished by combining body fluids or cell extracts taken from normal subjects, either animal or human, with antibody to HHP under conditions suitable for complex formation which are well known in the art. The amount of standard complex formation may be quantified by comparing various artificial membranes containing known quantities of HHP with both control and disease samples from biopsied tissues. Then, standard values obtained from normal samples may be compared with values obtained from samples from subjects potentially affected by disease. Deviation between standard and subject values establishes the presence of disease state.

Drug Screening

HHP, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between HHP and the agent being tested, may be measured.

Another technique for drug screening which provides for high throughput screening of compounds having suitable binding affinity to the HHP is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of HHP and washed. Bound HHP is then detected by methods well known in the art. Substantially purified HHP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding HHP specifically compete with a test compound for binding HHP. In this manner, the antibodies can be used to detect the presence of any peptide which shares one or more antigenic determinants with HHP.

Uses of the Polynucleotide Encoding HHP

A polynucleotide, hhp, or any part thereof, may be used for diagnostic and/or therapeutic purposes. For diagnostic purposes, the hhp of this invention may be used to detect and quantitate gene expression in biopsied tissues in which expression of HHP may be implicated. The diagnostic assay is useful to distinguish between absence, presence, and excess expression of HHP and to monitor regulation of HHP levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding HHP or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring hhp, alleles or related sequences.

Probes may also be used for the detection of related sequences and should preferably contain at least 50% of the nucleotides from any of these HHP encoding sequences. The hybridization probes of the subject invention may be derived from the nucleotide sequence of SEQ ID NO:2 or from genomic sequence including promoter, enhancer elements and introns of the naturally occurring hhp. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for hhp DNAs include the cloning of nucleic acid sequences encoding HHP or HHP derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostics

Polynucleotide sequences encoding HHP may be used for the diagnosis of conditions or diseases with which the expression of HHP is associated. For example, polynucleotide sequences encoding HHP may be used in hybridization or PCR assays of fluids or tissues from biopsies to detect hhp expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The hhp nucleotide sequences disclosed herein provide the basis for assays that detect activation or induction associated with inflammation or disease. The hhp nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of hhp nucleotide sequences in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for hhp expression must be established. This is accomplished by combining body fluids or cell extracts taken from normal subjects, either animal or human, with hhp, or a portion thereof, under conditions suitable for hybridization or amplification. Standard hybridization may be quantified by comparing the values obtained for normal subjects with a dilution series of hhp run in the same experiment where a known amount of substantially purified hhp is used. Standard values obtained from normal samples may be compared with values obtained from samples from patients affected by hhp-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR as described in U.S. Pat. Nos. 4,683,195 and 4,965,188 provides additional uses for oligonucleotides based upon the hhp sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or calorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutics

Based upon its homology to gene encoding human PH-20 and its expression profile, the hhp polynucleotide disclosed herein may be useful in the treatment of disorders such as carcinomas of the head or neck, melanomas, and prostate cancer, and inflammatory conditions caused by asthma, arthritis, and other diseases.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense hhp. See, for example, the techniques described in Sambrook et al (supra) and Ausubel et al (supra).

The polynucleotides comprising full length cDNA sequence and/or its regulatory elements enable researchers to use hhp as an investigative tool in sense (Youssoufian H and HF Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding HHP can be turned off by transfecting a cell or tissue with expression vectors which express high levels of a desired hhp fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of hhp, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of hhp.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HHP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences for hhp disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for hhp can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price CM (1993; Blood Rev 7:127–34) and Trask BJ (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a hhp on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of HHP, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy.

Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that HHP or an HHP derivative can be delivered in a suitable formulation as a chemotherapeutic agent. Similarly, administration of agonists should also improve the activity or lifespan of this protein and lessen the onset and progression of various cancers.

The examples below are provided to illustrate the subject invention and are not included for the purpose of limiting the invention.

EXAMPLES

I cDNA Library Construction

The rheumatoid knee synovium was removed from a 62 year-old female and used for cDNA library construction. The frozen tissue was homogenized using a Brinkmann Homogenizer Polytron PT-3000 (Brinkmann Instruments, Westbury N.J.) and lysed in a buffer containing guanidinium isothiocyanate. The lysate was centrifuged over a 5.7M CsCl cushion using an Beckman SW28 rotor in a Beckman L8–70M Ultracentrifuge (Beckman Instruments) for 18 hours at 25,000 rpm at ambient temperature. The RNA was extracted twice with acid phenol pH 4.0 using the reagents and extraction procedures supplied in the Stratagene RNA Isolation Kit (Catalog #1200345; Stratagene). RNA was precipitated using 0.3M sodium acetate and 2.5 volumes of ethanol, resuspended in water, and DNase treated for 15 min at 37° C. The RNA was isolated using the Qiagen Oligotex kit (QIAGEN Inc, Chatsworth Calif.).

The poly-$A^+$ RNA was handled according to the recommended protocols in the SuperScript Plasmid System for cDNA Synthesis and Plasmid Cloning (Catalog #18248–013; Gibco/BRL). First strand cDNA synthesis was accomplished using oligo d(T) priming and second strand synthesis was performed using a combination of DNA polymerase I, *E. coli* ligase and RNase H. The cDNA was blunted with T4 polymerase, and a Sal I linker was added to the blunt ended cDNA. The Sal I adapted, double-stranded cDNAs were the digested with Not I and fractionated on a Sepharose CL4B column (Catalog #275105, Pharmacia). Those cDNAs exceeding 400 bp were ligated into the plasmid pSport I which was subsequently transformed into DH5a™ competent cells (Catalog #118258–012, Gibco/BRL).

II Isolation and Sequencing of cDNA Clones

Plasmid DNA was released from the cells and substantially purified using the Miniprep Kit (Catalog #77468; Advanced Genetic Technologies Corporation, Gaithersburg Md.). This kit consists of a 96-well block with reagents for 960 purifications. The recommended protocol was employed except for the following changes: 1) the 96 wells were each filled with only 1 ml of sterile Terrific Broth (Catalog #22711, LIFE TECHNOLOGIES™) with carbenicillin at 25 mg/L and glycerol at 0.4%; 2) the bacteria were cultured for 24 hours after the wells were inoculated and then lysed with 60 $\mu$l of lysis buffer; 3) a centrifugation step employing the Beckman GS-6R rotor at 2900 rpm for 5 minutes was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems, and the reading frame was determined.

III Homology Searching of cDNA Clones and Their Deduced Proteins

Each cDNA was compared to sequences in GenBank using a search algorithm developed by Applied Biosystems and incorporated into the INHERIT670 Sequence Analysis System. In this algorithm, Pattern Specification Language (TRW Inc, Los Angeles Cailf.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul SF (1993) J Mol Evol 36:290–300; Altschul, SF et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Iv Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques using BLAST (Altschul SF 1993 and 1990, supra) are used to search for identical or related molecules in nucleotide databases such as GenBank or the LIFESEQ™ database (Incyte, Palo Alto Cailf.). This analysis is much faster than multiple, membrane-based hybridizations. In addition, the sensitivity of the computer search can be modified to determine whether any particular match is categorized as exact or homologous.

The basis of the search is the product score which is defined as:

% sequence identity×% maximum BLAST score and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of HHP to Full Length or to Recover Regulatory Elements

The nucleic acid sequence of full length hhp (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known hhp sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook J et al, supra). After incubation for one hour at 37° C., the whole transformation mixture is plated on Luria Bertani (LB)-agar (Sambrook J et al, supra) containing 2xCarb. The following day, several colonies are randomly picked from each plate and cultured in 150 μl of liquid LB/2xCarb medium placed in an individual well of an appropriate, commercially-available, sterile 96-well microtiter plate.

The following day, 5 μl of each overnight culture is transferred into a nonsterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [γ-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1 x saline sodium citrate and 0.5% sodium dodecyl sulfate. After XOMAT AR™ film (Kodak, Rochester N.Y.) is exposed to the blots in a Phosphoimager cassette (Molecular Dynamics,—Sunnyvale Cailf.) for several hours, hybridization patterns are compared visually.

VII Antisense Molecules

The hhp sequence, or any part thereof, is used to inhibit in vivo or in vitro expression of naturally occurring HHP.

Although use of antisense oligonucleotides, comprising about 20 base-pairs, is specifically described, essentially the same procedure is used with larger cDNA fragments. An oligonucleotide based on the coding sequence of HHP as shown in FIGS. 1A, 1B, 1C, and 1D is used to inhibit expression of naturally occurring HHP. The complementary oligonucleotide is designed from the most unique 5' sequence as shown in FIGS. 1A, 1B, 1C, and 1D and used either to inhibit transcription by preventing promoter binding to the upstream nontranslated sequence or translation of an hhp transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A, 1B, 1C, and 1D.

VIII Expression of HHP

Expression of the HHP is accomplished by subcloning the cDNAs into appropriate vectors and transfecting the vectors into host cells. In this case, the cloning vector, pSport, previously used for the generation of the cDNA library is used to express HHP in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length HHP. The signal sequence directs the secretion of HHP into the bacterial growth media which can be used directly in the following assay for activity.

IX HHP Activity

HHP activity can be measured by following the rates of hydrolysis of HA adsorbed onto microtiter wells. Following enzymatic digestion, the remaining HA can be measured using a cartilage-derived biotinylated HA-binding protein and an avidin-peroxidase reaction (Afify AM et al (1993) Arch Biochem Biophys 305: 434–441).

X Production of HHP Specific Antibodies

HHP substantially purified using PAGE electrophoresis (Sambrook, supra) is used to immunize rabbits and to produce antibodies using standard protocols. The amino acid sequence translated from HHP is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIGS. 4 and 5) is described by Ausubel F M et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HHP Using Specific Antibodies

Naturally occurring or recombinant HHP is substantially purified by immunoaffinity chromatography using antibodies specific for HHP. An immunoaffinity column is constructed by covalently coupling HHP antibody to an activated chromatographic resin such as CnBr-activated Sepharose (Pharmacia Biotech). After the coupling, the resin is blocked and washed according to the manufacturer's instructions.

Media containing HHP is passed over the immunoaffinity column, and the column is washed under conditions that allow the preferential absorbance of HHP (eg, high ionic strength buffers in the presence of detergent). The column is eluted under conditions that disrupt antibody/HHP binding (eg, a buffer of pH 2–3 or a high concentration of a chaotrope such as urea or thiocyanate ion), and HHP is collected.

XII Identification of Molecules Which Interact with HHP

HHP, or biologically active fragments thereof, are labelled with $^{125}$I Bolton-Hunter reagent (Bolton, AE and Hunter, WM (1973) Biochem J 133: 529). Candidate molecules previously arrayed in the wells of a 96 well plate are incubated with the labelled HHP, washed and any wells with labelled HHP complex are assayed. Data obtained using different concentrations of HHP are used to calculate values for the number, affinity, and association of HHP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A substantially purified polynucleotide encoding a polypeptide consisting of the amino acid sequence shown in SEQ ID NO: 1.

2. The polynucleotide of claim 1 wherein the nucleic acid sequence consists of SEQ ID NO:2, or its complement.

3. An expression vector comprising the polynucleotide of claim 1.

4. A host cell transformed with the expression vector of claim 3.

5. A method of producing a polypeptide consisting of the amino acid sequence shown in SEQ ID NO: 1, the method comprising the steps of:

a) culturing the host cell of claim 4 to allow the expression of the polypeptide; and b) recovering the polypeptide from the host cell culture.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
(A) LENGTH: 434 amino acids (B) TYPE: amino acid
(C) STRANDEDNESS: single
(D) TOPOLOGY: linear (ii) MOLECULE TYPE: peptide (vii) IMMEDIATE SOURCE:
(A) LIBRARY: SYNORAT04
(B) CLONE: 705483

(xi) SEQUENCE DESCRIPTION: SEQ ID NO:1:

```
Met Arg Ala Gly Pro Gly Pro Thr Val Thr Leu Ala Leu Val Leu Ala
 1               5                  10                  15

Val Xaa Trp Ala Met Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Leu Ser Thr Leu Arg Phe Cys Arg Lys Val Cys
                85                  90                  95

Ala Trp Trp Leu Cys His Arg Met Ser Gly Leu Trp Ala His Arg Lys
            100                 105                 110

Asn Ala Ala Glu Thr Cys Gly Ala Leu His Ser Gly His Thr Ser Leu
        115                 120                 125

Thr Gly Leu Ala Val Ile Asp Trp Glu Asp Trp Arg Pro Val Trp Val
    130                 135                 140

Arg Asn Trp Gln Asp Lys Asp Val Tyr Arg Arg Leu Ser Arg Gln Leu
145                 150                 155                 160

Val Ala Ser Arg His Pro Asp Trp Pro Pro Asp Arg Ile Val Lys Gln
                165                 170                 175

Ala Gln Tyr Glu Phe Glu Phe Ala Ala Gln Gln Phe Met Leu Glu Thr
            180                 185                 190

Leu Arg Tyr Val Lys Ala Val Arg Pro Arg His Leu Trp Gly Phe Tyr
        195                 200                 205

Leu Phe Pro Asp Cys Tyr Asn His Asp Tyr Val Gln Asn Trp Glu Ser
    210                 215                 220

Tyr Thr Gly Arg Cys Pro Asp Val Glu Val Ala Arg Asn Asp Gln Leu
225                 230                 235                 240

Ala Trp Leu Trp Ala Glu Ser Thr Ala Leu Phe Pro Ser Val Tyr Leu
                245                 250                 255

Asp Glu Thr Leu Ala Ser Ser Arg His Gly Arg Asn Phe Val Ser Phe
            260                 265                 270

Arg Val Gln Glu Ala Leu Arg Val Ala Arg Thr His His Ala Asn His
        275                 280                 285

Ala Leu Pro Val Tyr Val Phe Thr Arg Pro Thr Tyr Ser Arg Arg Leu
    290                 295                 300

Thr Gly Leu Ser Glu Met Asp Leu Ile Ser Thr Ile Gly Glu Ser Ala
305                 310                 315                 320

Ala Leu Gly Ala Ala Gly Val Ile Leu Trp Gly Asp Ala Gly Tyr Thr
                325                 330                 335

Thr Ser Thr Glu Thr Cys Gln Tyr Leu Lys Asp Tyr Leu Thr Arg Leu
            340                 345                 350

Leu Val Pro Tyr Val Val Asn Val Ser Trp Ala Thr Gln Tyr Cys Ser
        355                 360                 365
```

```
Arg Ala Gln Cys His Gly His Gly Arg Cys Val Arg Arg Asn Pro Ser
    370                 375                 380

Ala Ser Thr Phe Leu His Leu Ser Thr Asn Ser Phe Arg Leu Val Pro
385                 390                 395                 400

Gly His Ala Pro Gly Glu Pro Gln Leu Arg Pro Val Gly Glu Leu Ser
                405                 410                 415

Trp Ala Asp Ile Asp His Leu Gln Thr His Phe Arg Cys Gln Cys Thr
            420                 425                 430

Leu Ala
```

(2) INFORMATION FOR SEQ ID NO:2:

(i) SEQUENCE CHARACTERISTICS:
(A) LENGTH: 1450 base pairs
(B) TYPE: nucleic acid
(C) STRANDEDNESS: single
(D) TOPOLOGY: linear (ii) MOLECULE TYPE: cDNA (vii) IMMEDIATE SOURCE:
(A) LIBRARY: SYNORAT04
(B) CLONE: 705483

(xi) SEQUENCE DESCRIPTION: SEQ ID NO:2:

```
ACTGGAGAGG CTCAGGCCAG GCAAGGAAGG AGGCCACCGA CCTACTGGGC CGACGGACTC     60

CCACACAGTT CCTGAGCTGG TGCCAGGCAG GTGACACCTC CTGCAGCCCC CAGCATGCGG    120

GCAGGCCCAG GCCCCACCGT TACATTGGCC CTGGTGCTGG CGGTGKCATG GGCCATGGAG    180

CTCAAGCCCA CAGCACCACC CATCTTCACT GGCCGGCCCT TTGTGGTAGC GTGGGACGTG    240

CCCACACAGG ACTGTGGCCC ACGCCTCAAG GTGCCACTGG ACCTGAATGC CTTTGATGTG    300

CAGGCCTCAC CTAATGAGGG TTTTGTGAAC CAGAATATTA CCATCTTCTA CCGCGACCGT    360

CTAGGCCTGT TATCCACGCT TCGATTCTGC CGGAAGGTCT GTGCATGGTG GTTGTGCCAC    420

AGAATGTCAG GCCTTTGGGC ACACCGGAAG AATGCTGCAG AAACGTGTGG AGCACTACAT    480

TCGGGACACA CGAGTCTGAC GGGGCTGGCG GTCATCGACT GGGAGGACTG GCGACCTGTG    540

TGGGTGCGCA ACTGGCAGGA CAAAGATGTG TATCGCCGGT TATCACGCCA GCTAGTGGCC    600

AGTCGTCACC CTGACTGGCC TCCAGACCGC ATAGTCAAAC AGGCACAATA TGAGTTTGAG    660

TTCGCAGCAC AGCAGTTCAT GCTGGAGACA CTGCGTTATG TCAAGGCAGT GCGGCCCCGG    720

CACCTCTGGG GCTTCTACCT CTTTCCTGAC TGCTACAATC ATGATTATGT GCAGAACTGG    780

GAGAGCTACA CAGGCCGCTG CCCTGATGTT GAGGTGGCCC GCAATGACCA GCTGGCCTGG    840

CTGTGGGCTG AGAGCACGGC CCTCTTCCCG TCTGTCTACC TGGACGAGAC ACTTGCTTCC    900

TCCCGCCATG GCCGCAACTT TGTGAGCTTC CGTGTTCAGG AGGCCCTTCG TGTGGCTCGC    960

ACCCACCATG CCAACCATGC ACTCCCAGTC TACGTCTTCA CACGACCCAC CTACAGCCGC   1020

AGGCTCACGG GGCTTAGTGA GATGGACCTC ATCTCTACCA TTGGCGAGAG TGCGGCCCTG   1080

GGCGCAGCTG GTGTCATCCT CTGGGGTGAC GCGGGGTACA CCACAAGCAC GGAGACCTGC   1140

CAGTACCTCA AAGATTACCT GACACGGCTG CTGGTCCCCT ACGTGGTCAA TGTGTCCTGG   1200

GCCACCCAAT ATTGCAGCCG GGCCCAGTGC CATGGCCATG GGCGCTGTGT GCGCCGCAAC   1260

CCCAGTGCCA GTACCTTCCT GCATCTCAGC ACCAACAGTT TCCGCCTAGT GCCTGGCCAT   1320

GCACCTGGTG AACCCCAGCT GCGACCTGTG GGGGAGCTCA GTTGGGCCGA CATTGACCAC   1380
```

```
CTGCAGACAC ACTTCCGCTG CCAGTGTACT TTGGCTTGAG TGGTTAGCAA TGCCAATNGG   1440

ACCATAGGCA                                                          1450
```

(2) INFORMATION FOR SEQ ID NO:3:

(i) SEQUENCE CHARACTERISTICS:
(A) LENGTH: 509 amino acids
(B) TYPE: amino acid
(C) STRANDEDNESS: single
(D) TOPOLOGY: linear (ii) MOLECULE TYPE: peptide (vii) IMMEDIATE SOURCE:
(A) LIBRARY: GenBank
(B) CLONE: 585674

(xi) SEQUENCE DESCRIPTION: SEQ ID NO:3:

```
Met Gly Val Leu Lys Phe Lys His Ile Phe Phe Arg Ser Phe Val Lys
 1               5                  10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Ala
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320
```

```
Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
            500                 505
```

(2) INFORMATION FOR SEQ ID NO:4:

(i) SEQUENCE CHARACTERISTICS:
(A) LENGTH: 512 amino acids
(B) TYPE: amino acid
(C) STRANDEDNESS: single
(D) TOPOLOGY: linear (ii) MOLECULE TYPE: peptide (vii) IMMEDIATE SOURCE:
(A) LIBRARY: GenBank
(B) CLONE: 998338

(xi) SEQUENCE DESCRIPTION: SEQ ID NO:4:

```
Met Gly Glu Leu Arg Phe Lys His Leu Phe Trp Gly Ser Phe Val Glu
 1               5                  10                  15

Ser Gly Gly Thr Phe Gln Thr Val Leu Ile Phe Leu Leu Ile Pro Cys
            20                  25                  30

Ser Leu Thr Val Asp Tyr Arg Ala Ala Pro Ile Leu Ser Asn Thr Thr
        35                  40                  45

Phe Leu Trp Ile Trp Asn Val Pro Thr Glu Arg Cys Val Gly Asn Val
    50                  55                  60

Asn Asp Pro Ile Asp Leu Ser Phe Phe Ser Leu Ile Gly Ser Pro Arg
65                  70                  75                  80

Lys Thr Ala Thr Gly Gln Pro Val Thr Leu Phe Tyr Val Asp Arg Leu
                85                  90                  95

Gly Leu Tyr Pro His Ile Asp Ala Asn Gln Ala Glu His Tyr Gly Gly
            100                 105                 110
```

-continued

```
Ile Pro Gln Arg Gly Asp Tyr Gln Ala His Leu Arg Lys Ala Lys Thr
        115                 120                 125

Asp Ile Glu His Tyr Ile Pro Asp Asp Lys Leu Gly Leu Ala Ile Ile
    130                 135                 140

Asp Trp Glu Glu Trp Arg Pro Thr Trp Leu Arg Asn Trp Lys Pro Lys
145                 150                 155                 160

Asp Asn Tyr Arg Asn Lys Ser Ile Glu Leu Val Gln Ser Thr Asn Pro
                165                 170                 175

Gly Leu Ser Ile Thr Arg Ala Thr Gln Lys Ala Ile Gln Gln Leu Glu
            180                 185                 190

Glu Ala Gly Arg Lys Phe Met Glu Gly Thr Leu His Leu Gly Lys Phe
        195                 200                 205

Leu Arg Pro Asn Gln Leu Trp Gly Tyr Tyr Leu Phe Pro Asp Cys Tyr
    210                 215                 220

Asn Asn Lys Phe Gln Asp Pro Lys Tyr Asp Gly Gln Cys Pro Ala Val
225                 230                 235                 240

Glu Lys Lys Arg Asn Asp Asn Leu Lys Trp Leu Trp Lys Ala Ser Thr
                245                 250                 255

Gly Leu Tyr Pro Ser Val Tyr Leu Lys Lys Asp Leu Lys Ser Asn Arg
            260                 265                 270

Gln Ala Thr Leu Tyr Val Arg Tyr Arg Val Val Glu Ala Ile Arg Val
        275                 280                 285

Ser Lys Val Gly Asn Ala Ser Asp Pro Val Pro Ile Phe Val Tyr Ile
    290                 295                 300

Arg Leu Val Phe Thr Asp Arg Thr Ser Glu Tyr Leu Leu Glu Asp Asp
305                 310                 315                 320

Leu Val Asn Thr Ile Gly Glu Ile Val Ala Leu Gly Thr Ser Gly Ile
                325                 330                 335

Ile Ile Trp Asp Ala Met Ser Leu Ala Gln Arg Ala Ala Gly Cys Pro
            340                 345                 350

Ile Leu His Lys Tyr Met Gln Thr Thr Leu Asn Pro Tyr Ile Val Asn
        355                 360                 365

Val Thr Leu Ala Ala Lys Met Cys Ser Gln Thr Leu Cys Asn Glu Lys
    370                 375                 380

Gly Met Cys Ser Arg Arg Lys Glu Ser Ser Asp Val Tyr Leu His Leu
385                 390                 395                 400

Asn Pro Ser His Phe Asp Ile Met Leu Thr Glu Thr Gly Lys Tyr Glu
                405                 410                 415

Val Leu Gly Asn Pro Arg Val Gly Asp Leu Glu Tyr Phe Ser Glu His
            420                 425                 430

Phe Lys Cys Ser Cys Phe Ser Arg Met Thr Cys Lys Glu Thr Ser Asp
        435                 440                 445

Val Lys Asn Val Gln Asp Val Asn Val Cys Val Gly Asp Asn Val Cys
    450                 455                 460

Ile Lys Ala Lys Val Glu Pro Asn Pro Ala Phe Tyr Leu Leu Pro Gly
465                 470                 475                 480

Lys Ser Leu Leu Phe Met Thr Thr Leu Gly His Val Leu Tyr His Leu
                485                 490                 495

Pro Gln Asp Ile Phe Val Phe Pro Arg Lys Thr Leu Val Ser Thr Pro
            500                 505                 510
```

(2) INFORMATION FOR SEQ ID NO:5:

(i) SEQUENCE CHARACTERISTICS:
(A) LENGTH: 331 amino acids

-continued (B) TYPE: amino acid
(C) STRANDEDNESS: single
(D) TOPOLOGY: linear (ii) MOLECULE TYPE: peptide (vii) IMMEDIATE SOURCE:
(A) LIBRARY: GenBank
(B) CLONE: 1362656

(xi) SEQUENCE DESCRIPTION: SEQ ID NO:5:

```
Ser Glu Arg Pro Lys Arg Val Phe Asn Ile Tyr Trp Asn Val Pro Thr
 1               5                  10                  15

Phe Met Cys His Gln Tyr Gly Leu Tyr Phe Asp Glu Val Thr Asn Phe
            20                  25                  30

Asn Ile Lys His Asn Ser Lys Asp Asp Phe Gln Gly Asp Lys Ile Ser
        35                  40                  45

Ile Phe Tyr Asp Pro Gly Glu Phe Pro Ala Leu Leu Pro Leu Lys Glu
    50                  55                  60

Gly Asn Tyr Lys Ile Arg Asn Gly Gly Val Pro Gln Glu Gly Asn Ile
65                  70                  75                  80

Thr Ile His Leu Gln Arg Phe Ile Glu Asn Leu Asp Lys Thr Tyr Pro
                85                  90                  95

Asn Arg Asn Phe Asn Gly Ile Gly Val Ile Asp Phe Glu Arg Trp Arg
            100                 105                 110

Pro Ile Phe Arg Gln Asn Trp Gly Asn Met Met Ile His Lys Lys Phe
        115                 120                 125

Ser Ile Asp Leu Val Arg Asn Glu His Pro Phe Trp Asp Lys Lys Met
    130                 135                 140

Ile Glu Leu Glu Ala Ser Lys Arg Phe Glu Lys Tyr Ala Arg Leu Phe
145                 150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
            180                 185                 190

Leu Val Pro Asp Cys Asp Ala Thr Ala Met Leu Glu Asn Asp Lys Met
        195                 200                 205

Ser Trp Leu Phe Asn Asn Gln Asn Val Leu Leu Pro Ser Val Tyr Ile
    210                 215                 220

Arg His Glu Leu Thr Pro Asp Gln Arg Val Gly Leu Val Gln Gly Arg
225                 230                 235                 240

Val Lys Glu Ala Val Arg Ile Ser Asn Asn Leu Lys His Ser Pro Lys
                245                 250                 255

Val Leu Ser Tyr Trp Trp Tyr Val Tyr Gln Asp Asp Thr Asn Thr Phe
            260                 265                 270

Leu Thr Glu Thr Asp Val Lys Lys Thr Phe Gln Glu Ile Ala Ile Asn
        275                 280                 285

Gly Gly Asp Gly Ile Ile Ile Trp Gly Ser Ser Ser Asp Val Asn Ser
    290                 295                 300

Leu Ser Lys Cys Lys Arg Leu Arg Glu Tyr Leu Leu Thr Val Leu Gly
305                 310                 315                 320

Pro Ile Thr Val Asn Val Thr Glu Thr Val Asn
                325                 330
```